United States Patent
Gamache et al.

(10) Patent No.: US 6,638,976 B2
(45) Date of Patent: Oct. 28, 2003

(54) METHOD OF TREATING NEURODEGENERATIVE DISORDERS OF THE RETINA AND OPTIC NERVE HEAD

(75) Inventors: Daniel A. Gamache, Arlington, TX (US); Gustav Graff, Cleburne, TX (US); John M. Yanni, Burleson, TX (US); Michael A. Kapin, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 09/929,704

(22) Filed: Aug. 13, 2001

(65) Prior Publication Data

US 2002/0049255 A1 Apr. 25, 2002

Related U.S. Application Data

(60) Provisional application No. 60/225,132, filed on Aug. 14, 2000.

(51) Int. Cl.$^7$ .............................................. A61K 31/216
(52) U.S. Cl. .................. 514/532; 514/534; 514/561; 514/562; 514/563; 514/564; 514/617; 514/618; 514/619
(58) Field of Search ................................ 514/532, 534, 514/561, 562, 563, 564, 617, 618, 619

(56) References Cited

U.S. PATENT DOCUMENTS

| | | | |
|---|---|---|---|
| 3,828,093 A | 8/1974 | Bays et al. ................. | 260/469 |
| 4,045,576 A | 8/1977 | Welstead, Jr. et al. ...... | 424/309 |
| 4,126,635 A | 11/1978 | Welstead, Jr. et al. ...... | 562/441 |
| 4,182,774 A | 1/1980 | Welstead, Jr. et al. ...... | 424/309 |
| 4,254,146 A | 3/1981 | Walsh ........................ | 424/309 |
| 4,313,949 A | 2/1982 | Shanklin, Jr. et al. .. | 424/248.56 |
| 4,454,151 A | 6/1984 | Waterbury .................. | 424/274 |
| 4,503,073 A | 3/1985 | Walsh et al. ................ | 514/539 |
| 4,568,695 A | 2/1986 | Moran et al. ............... | 514/648 |
| 4,683,242 A | 7/1987 | Poser ......................... | 514/539 |
| 4,783,487 A | 11/1988 | Brune ........................ | 514/563 |
| 4,851,443 A | 7/1989 | Brune ........................ | 514/563 |
| 4,910,225 A | 3/1990 | Ogawa et al. .............. | 514/561 |
| 5,073,641 A | 12/1991 | Bundgaard et al. .......... | 560/56 |
| 5,314,909 A | 5/1994 | Dollerup .................... | 514/420 |
| 5,475,034 A | 12/1995 | Yanni et al. ................ | 514/619 |
| 5,811,438 A * | 9/1998 | Hellberg et al. ............ | 514/458 |
| 5,811,446 A | 9/1998 | Thomas ...................... | 514/399 |
| 6,025,353 A | 2/2000 | Masferrer et al. .......... | 514/210 |
| 6,066,671 A | 5/2000 | Yanni et al. ................ | 514/619 |
| 6,069,139 A | 5/2000 | Kuriyama et al. .......... | 514/100 |
| 6,342,524 B1 | 1/2002 | Hellberg et al. ............ | 514/530 |

FOREIGN PATENT DOCUMENTS

| | | | |
|---|---|---|---|
| DE | 3026402 | * | 2/1982 |
| EP | 0 326 915 A1 | | 8/1989 |
| EP | 1 064 949 A2 | | 1/2001 |
| EP | 1 064 964 A2 | | 1/2001 |
| EP | 1 064 965 A2 | | 1/2001 |
| GB | 2 071 086 A | | 9/1981 |
| GB | 2 093 027 A | | 8/1982 |
| WO | WO 00/40087 | | 7/2000 |
| WO | WO 01/28474 A1 | | 4/2001 |

OTHER PUBLICATIONS

Rawji et al., "Quantification of Concanavalin–A Mediated Retinal Edema Using Scanning Laser Tomography Derived Edema Maps," *Investigative, Ophthalmology. And Visual. Science, The Association for Research in Vision and Ophthalmology*, vol. 41(4):871 (2000).

Sancilio et al., "AHR–10037, a non–steroidal anti–inflammatory compound of low gastric toxicity," *Agents and Actions*, vol. 31(1/2), pp. 117–126 (1990).

Walsh et al., "Antiinflammatory Agents. 4. Syntheses and Biological Evaluation of Potential Prodrugs of 2–Amino–3–benzoylbenzeneacetic Acid and 2–Amino–3–(4–chlorobenzoyl)benzeneacetic Acid," *J. Med. Chem.*, vol. 33, pp. 2296–2304 (1990).

Walsh et al., "Antiinflammatory Agents. 3. Syntheses and Pharmacological Evaluation of 2–Amino–3–benzoylphenylacetic Acid and Analogues," *J. Med. Chem.*, vol. 27(11), pp. 1379–1388 (1984).

Graff et al., "In Vitro Characterization of the Ocular Bioactivation and Permeation of External Ocular Barriers of Nepafenac, a Potent Topical Ocular NSAID with Long Duration of Action," *Investigative, Ophthalmology. And Visual. Science, The Association for Research in Vision and Ophthalmology*, vol. 41(4):1892 (2000).

Kapin et al., "Inhibition of Concanavalin–A Mediated Pan Retinal Edema By Nepafenac," *Investigative, Ophthalmology. And Visual. Science, The Association for Research in Vision and Ophthalmology*, vol. 41(4):1887 (2000).

Ke et al. "Nepafenac, A Unique Nonsteroidal Prodrug with Potential Utility in the Treatment of Trauma–Induced Ocular Inflammation: II. In Vitro Bioactivation and Permeation of External Ocular Barriers," *Inflammation*, vol. 24(4), pp. 371–384 (2000).

Clark et al., "Ocular Angiostatic Agents," *Exp. Opin. Ther. Patents*, vol. 10(4), pp. 427–448 (2000).

Gamache et al., "Nepafenac, A Unique Nonsteroidal Anti–Inflammatory Prodrug With Potential Utility In The Treatment Of Trauma–Induced Acute Ocular Inflammation," *Investigative, Ophthalmology. And Visual. Science, The Association for Research in Vision and Ophthalmology*, vol. 41(4):1892 (2000).

Gamache et al., "Nepafenac, A Unique Nonsteroidal Prodrug with Potential Utility in the Treatment of Trauma–Induced Ocular Inflammation: I. Assessment of Anti–Inflammatory Efficacy," *Inflammation*, Vol 24(4); pp. 357–370 (2000).

* cited by examiner

*Primary Examiner*—Phyllis G. Spivack
(74) *Attorney, Agent, or Firm*—Teresa J. Schultz

(57) ABSTRACT

The use of 3-benzolphenylacetic acids and derivatives, including nepafenac, to treat neurodegenerative retinal disorders is disclosed.

12 Claims, No Drawings

METHOD OF TREATING NEURODEGENERATIVE DISORDERS OF THE RETINA AND OPTIC NERVE HEAD

This application claims priority to U.S. Provisional Application, Serial No. 60/225,132, filed Aug. 14, 2000.

FIELD OF THE INVENTION

This invention relates to the treatment of retinopathy. In particular, this invention relates to the use of certain 3-benzoylphenylacetic acids and derivatives to treat or prevent neurodegenerative disorders of the retina and optic nerve head.

BACKGROUND OF THE INVENTION 3-benzoylphenylacetic acid and certain of its derivatives are known to possess anti-inflammatory activity. U.S. Pat. Nos. 4,254,146, 4,045,576, 4,126,635, and 4,503,073, and U.K. Patent Application Nos. 2,071,086A and 2,093,027A disclose various 3-benzoylphenylacetic acids, salts and esters, and hydrates thereof, having anti-inflammatory activity. U.S. Pat. No. 4,568,695 discloses 2-amino-3-benzoylphenylethyl alcohols having anti-inflammatory activity. U.S. Pat. No. 4,313,949 discloses 2-amino-3-benzoyl-phenylacetamides having anti-inflammatory activity.

Certain derivatives of 2-amino-3-benzoylbenzeneacetic acid (amfenac) and 2-amino-3-(4-chloro-benzoyl) benzeneacetic acid have also been evaluated by Walsh et al., J. Med Chem., 33:2296–2304 (1990), in an attempt to discover nonsteroidal anti-inflammatory prodrugs with minimal or no gastrointestinal side effects upon oral administration.

U.S. Pat. No. 4,683,242 teaches the transdermal administration of 2-amino-3-benzoylphenylacetic acids, salts, and esters, and hydrates and alcoholates thereof to control inflammation and alleviate pain.

U.S. Pat. No. 4,910,225 teaches certain benzoylphenylacetic acids for local administration to control ophthalmic, nasal or otic inflammation. Only acetic acids are disclosed in the '225 patent; no esters or amides are mentioned or taught as anti-inflammatory agents for local administration to the eyes, nose and ears.

U.S. Pat. No. 5,475,034 discloses topically administrable compositions containing certain amide and ester derivatives of 3-benzoylphenylacetic acid, including nepafenac, useful for treating ophthalmic inflammatory disorders and ocular pain. According to the '035 patent at Col. 15, lines 35–39, "[s]uch disorders include, but are not limited to uveitis, scleritis, episcleritis, keratitis, surgically-induced inflammation and endophthalmitis."

U.S. Pat. No. 6,066,671 discloses the topical use of certain amide and ester derivatives of 3-benzoylphenylacetic acid, including nepafenac, for treating GLC1A glaucoma.

SUMMARY OF THE INVENTION

It has now been found that certain 3-benzoylphenylacetic acids and derivatives, including nepafenac (2-amino,3-benzoyl-phenylacetamide), are useful in treating neurodegenerative disorders of the retina and optic nerve head.

DETAILED DESCRIPTION OF THE INVENTION

The 3-benzoylphenylacetic acids and derivatives useful in the methods of the present invention are those of formula (I) below.

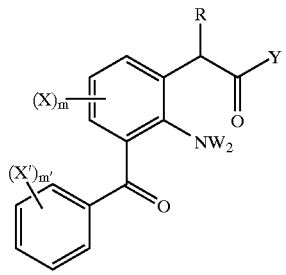

(I)

R=H, $C_{1-4}$ (un)branched alkyl, $CF_3$, $SR^4$

Y=OR', NR"R';

R'=H, $C_{1-10}$ (un)branched alkyl, (un)substituted aryl (substitution as defined by X below), (un)substituted heterocycle (substitution as defined by X below), —$(CH_2)_nZ(CH_2)_{n'}A$;

n=2–6;

n'=1–6;

Z=nothing, O, C=O, OC(=O), C(=O)O, C(=O)$NR^3$, $NR^3C(=O)$, $S(O)_{n^2}$, $CHOR^3$, $NR^3$;

$n^2$=0–2;

$R^3$=H, $C_{1-6}$ (un)branched alkyl, (un)substituted aryl (substitution as defined by X below), (un)substituted heterocycle (substitution as defined by X below)

A=H, OH, optionally (un)substituted aryl (substitution as defined by X below), (un)substituted heterocycle (substitution as defined by X below), —$(CH_2)_nOR^3$;

R"=H, OH, OR'

X and X' independently=H, F, Cl, Br, I, OR', CN, OH, $S(O)_{n^2}R^4$, $CF_3$, $R^4$, $NO_2$;

$R^4=C_{1-6}$ (un)branched alkyl;

m=0–3;

m'=0–5;

W=O, H.

As used herein, the acid (Y=OH) includes pharmaceutically acceptable salts as well.

Preferred compounds for use in the methods of the present invention are those of Formula I wherein:

R=H, $C_{1-2}$ alkyl;

Y=NR'R";

R'=H, $C_{1-6}$ (un)branched alkyl, —$(CH_2)_nZ(CH_2)_{n'}A$;

Z=nothing, O, $CHOR^3$, $NR^3$;

$R^3$=H;

A=H, OH, (un)substituted aryl (substitution as defined by X below);

X and X' independently=H, F, Cl, Br, CN, $CF_3$, OR', $SR^4$, $R^4$;

R"=H;

$R^4=C_{1-4}$ (un)branched alkyl;

m=0–2;

m'=0–2;

W=H;

n=2–4;

n'=0–3.

The most preferred compounds for use in the compositions or method of the present invention are 2-Amino-3-(4-fluorobenzoyl)-phenylacetamide; 2-Amino-3-benzoylphenylacetamide (nepafenac); and 2-Amino-3-(4-chlorobenzoyl)-phenylacetamide.

According to the present invention, a therapeutically effective amount of a compound of formula (I) is administered topically, locally or systemically to treat or prevent neurodegenerative disorders of the retina and optic nerve head. Such disorders include, but are not limited to atrophic macular degeneration; retinitis pigmentosa; iatrogenic retinopathy; retinal tears and holes; diabetic retinopathy; sickle cell retinopathy; retinal vein and artery occlusion; and optic neuropathy. Certain ophthalmic disorders, such as sickle cell retinopathy and retinal vein or artery occlusion, can be characterized by both angiogenesis and neurodegenerative components. According to the present invention, a compound of formula (I) is administered to treat or prevent disorders characterized, at least in part, by neurodegeneration.

The compounds of formula (I) can be administered in a variety of ways, including all forms of local delivery to the eye, such as subconjunctival injections or implants, intravitreal injections or implants, sub-Tenon's injections or implants, incorporation in surgical irrigating solutions, etc. Additionally, the compounds of formula (I) can be administered systemically, such as orally or intravenously. Suitable pharmaceutical vehicles or dosage forms for injectable compositions, implants, and systemic administration are known. The compounds of formula (I) and especially those wherein Y=NR'R", however, are preferably administered topically to the eye and can be formulated into a variety of topically administrable ophthalmic compositions, such as solutions, suspensions, gels or ointments.

Pharmaceutical compositions comprising a compound of formula (I) in aqueous solution or suspension, optionally containing a preservative for multidose use and other conventionally employed ophthalmic adjuvants, can be topically administered to the eye. The most preferred form of delivery is by aqueous eye drops, but gels or ointments can also be used. Aqueous eye drops, gels and ointments can be formulated according to conventional technology and would include one or more excipients. For example, topically administrable compositions may contain tonicity-adjusting agents, such as mannitol or sodium chloride; preservatives such as chlorobutanol, benzalkonium chloride, polyquaternium-1, or chlorhexidine; buffering agents, such as phosphates, borates, carbonates and citrates; and thickening agents, such as high molecular weight carboxy vinyl polymers, including those known as carbomers, hydroxyethylcellulose, or polyvinyl alcohol.

The doses of the compounds of formula (I) used in the treatment or prevention of neurodegenerative disorders of the retina and optic nerve head will depend on the type of disorder to be prevented or treated, the age and body weight of the patient, and the form of preparation/route of administration. Compositions intended for topical ophthalmic administration will typically contain a compound of formula (I) in an amount of from about 0.001 to about 4.0% (w/v), preferably from about 0.01 to about 0.5% (w/v), with 1–2 drops once to several times a day. Likewise, representative doses for other forms of preparations are approximately 1–100 mg/day/adult for injections and approximately 10–1000 mg/adult for oral preparations, each administered once to several times a day.

Additional therapeutic agents may be added to supplement the compounds of formula (I).

The following examples are presented to illustrate various aspects of the present invention, but are not intended to limit the scope of the invention in any respect. The percentages are expressed on a weight/volume basis.

EXAMPLE 1

The following formulations are representative of the topical compositions useful in the present invention.

| Formulation 1 | |
|---|---|
| Compound of formula (I) | 0.01–0.5% |
| Polysorbate 80 | 0.01% |
| Benzalkonium Chloride | 0.01% + 10% excess |
| Disodium EDTA | 0.1% |
| Monobasic Sodium Phosphate | 0.03% |
| Dibasic Sodium Phosphate | 0.1% |
| Sodium Chloride | q.s. 290–300 mOsm/Kg |
| pH adjustment with NaOH and/or HCl | pH 4.2–7.4 |
| Water | q.s. 100% |

| Formulation 2 | |
|---|---|
| Compound of formula (I) | 0.01–0.5% |
| Hydroxypropyl Methylcellulose | 0.5% |
| Polysorbate 80 | 0.01% |
| Benzalkonium Chloride | 0.01% + 5% excess |
| Disodium EDTA | 0.01% |
| Dibasic Sodium Phosphate | 0.2% |
| Sodium Chloride | q.s. 290–300 mOsm/Kg |
| pH adjustment with NaOH and/or HCl | pH 4.2–7.4 |
| Water | q.s. 100% |

| Formulation 3 | |
|---|---|
| Nepafenac | 0.1 + 6% excess |
| Carbopol 974P | 0.08% |
| Tyloxapol | 0.01% |
| Glycerin | 2.4% |
| Disodium EDTA | 0.01% |
| Benzalkonium Chloride | 0.01% |
| pH adjustment with NaOH and/or HCl | pH 7.5 ± 0.2 |
| Water | q.s. 100% |

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

We claim:

1. A method of treating or preventing a neurodegenerative disorder of the retina or optic nerve head in a patient suffering from or predisposed to such a disorder which comprises administering to the patient a therapeutically effective amount of 3-benzoylphenylacetic acid or derivative of the formula:

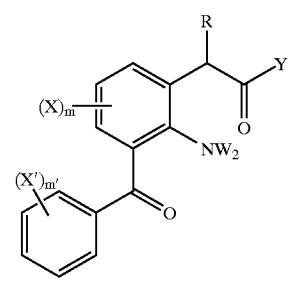

wherein
R=H, $C_{1-4}$ (un)branched alkyl, $CF_3$, $SR_4$;
Y=OR', NR"R';
R'=H, $C_{1-10}$ (un)branched alkyl, aryl, aryl substituted by X, heterocycle, heterocycle substituted by X, —$(CH_2)_nZ(CH_2)_{n'}$·A;
n=2–6;
n'=1–6;
Z=nothing, O, C=O, OC(=O), C(=O)O, C(=O)NR$^3$, NR$^3$C(=O), S(O)$_{n^2}$, CHOR$^3$, NR$^3$;
$n^2$=0–2;
R$^3$=H, $C_{1-6}$ (un)branched alkyl, aryl, aryl substituted by X, heterocycle, heterocycle substituted by X;
A=H, OH, aryl, aryl substituted by X, heterocycle, heterocycle substituted by X, —$(CH_2)_nOR^3$;
R"=H, OH, OR';
X and X' independently=H, F, Cl, Br, I, OR', CN, OH, S(O)$_{n^2}$R$^4$, CF$_3$, R$^4$, NO$_2$;
R$^4$=$C_{1-6}$ (un)branched alkyl;
m=0–3;
m'=0–5; and
W=O, H.

2. The method of claim 1 wherein
R=H, $C_{1-2}$ alkyl;
Y=NR'R";
R'=H, $C_{1-6}$ (un)branched alkyl, —$(CH_2)_nZ(CH_2)_{n'}$A;
Z=nothing, O, CHOR$^3$, NR$^3$;
R$_3$=H;
A=H, OH, aryl, aryl substituted by X;
X and X' independently=H, F, Cl, Br, CN, CF$_3$, OR', SR$^4$, R$^4$;
R"=H;
R$^4$=$C_{1-4}$ (un)branched alkyl;
m=0–2;
m'=0–2;
W=H;
n=2–4; and
n'=0–3.

3. The method of claim 2 wherein the 3-benzoylphenylacetic acid or derivative is selected from the group consisting of 2-Amino-3-(4-fluorobenzoyl)-phenylacetamide; 2-Amino-3-benzoyl-phenylacetamide; and 2-Amino-3-(4-chlorobenzoyl)-phenylacetamide.

4. The method of claim 1 wherein the 3-benzoylphenylacetic acid or derivative is topically administered to the eye.

5. The method of claim 4 wherein the therapeutically effective amount of 3-benzoylphenylacetic acid or derivative is from about 0.001 to about 4.0% (w/v).

6. The method of claim 1 wherein the 3-benzoylphenylacetic acid or derivative is administered orally, intravenously, in a subconjunctival injection or implant, in a sub-Tenon's injection or implant, in an intravitreal injection or implant, or in a surgical irrigating solution.

7. A method of providing neuroprotection to the retina or optic nerve head in a patient suffering from or predisposed to a neurodegenerative disorder of the retina or optic nerve head said method comprising administering to the patient a therapeutically effective amount of 3-benzoylphenylacetic acid or derivative of the formula:

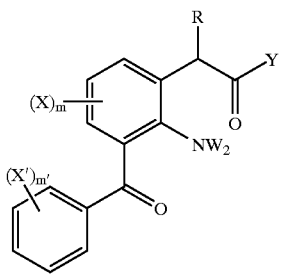

wherein
R =H, $C_{1-4}$ (un)branched alkyl, $CF_3$, SR$^4$
Y=OR', NR"R';
R'=H, $C_{1-10}$ (un)branched alkyl, alkyl substituted by X, heterocycle, heterocycle substituted by X, —$(CH_2)_nZ(CH_2)_{n'}$A;
n=2–6;
n'=1–6;
Z=nothing, O, C=O, OC(=O), C(=O)O, C(=O)NR$^3$, NR$^3$C(=O), S(O)$_{n^2}$, CHOR$^3$, NR$^3$;
$n^2$=0–2;
R$^3$=H, $C_{1-6}$ (un)branched alkyl, aryl, aryl substituted by X, heterocycle, heterocycle substituted by X;
A=H, OH, aryl, aryl substituted by X, heterocycle, heterocycle substituted by X, —$(CH_2)_nOR^3$,
R"=H, OH, OR';
X and X' independently=H, F, Cl, Br, I, OR', CN, OH, S(O)$_{n^2}$R$^4$, CF$_3$, R$^4$, NO$_2$;
R$^4$=$C_{1-6}$ (un)branched alkyl;
m=0–3;
m'=0–5; and
W=O, H;
wherein the disorder is selected from the group consisting of atrophic macular degeneration;
retinitis pigmentosa;
iatrogenic retinopathy;
retinal tears and holes;
diabetic retinopathy;
sickle cell retinopathy;
retinal vein and artery occlusion; and
optic neuropathy.

8. The method of claim 7 wherein
R=H, $C_{1-2}$ alkyl;
Y=NR'R";
R'=H, $C_{1-6}$ (un)branched alkyl,—$(CH_2)_nZ(CH_2)_{n'}$A;
Z=nothing, O, CHOR$^3$, NR$^3$;
R$_3$=H;
A=H, OH, aryl, aryl substituted by X;
X and X' independently=H, F, Cl, Br, CN, CF$_3$, OR', SR$^4$, R$^4$;
R"=H;
R$^4$=$C_{1-4}$ (un)branched alkyl;
m=0–2;
m'=0–2;
W=H;
n=2–4; and
n'=0–3.

9. The method of claim 8 wherein the 3-benzoylphenylacetic acid or derivative is selected from the group consisting of 2-Amino-3-(4-fluorobenzoyl)-phenylacetamide;

2-Amino-3-benzoyl-phenylacetamide; and

2-Amino-3-(4-chlorobenzoyl)-phenylacetamide.

10. The method of claim 7 wherein the 3-benzoylphenylacetic acid or derivative is topically administered to the eye.

11. The method of claim 10 wherein the therapeutically effective amount of 3-benzoylphenylacetic acid or derivative is from about 0.001 to about 4.0% (w/v).

12. The method of claim 7 wherein the 3-benzoylphenylacetic acid or derivative is administered orally, intravenously, in a subconjunctival injection or implant, in a sub-Tenon's injection or implant, in an intravitreal injection or implant, or in a surgical irrigating solution.

* * * * *

UNITED STATES PATENT AND TRADEMARK OFFICE
CERTIFICATE OF CORRECTION

PATENT NO.    : 6,638,976 B2  
DATED         : October 28, 2003  
INVENTOR(S)   : Gamache et al.

It is certified that error appears in the above-identified patent and that said Letters Patent is hereby corrected as shown below:

Column 5,  
Line 2, delete "$SR_4$" and add -- $SR^4$ --.

Signed and Sealed this

Second Day of March, 2004

JON W. DUDAS  
*Acting Director of the United States Patent and Trademark Office*

UNITED STATES PATENT AND TRADEMARK OFFICE
CERTIFICATE OF CORRECTION

PATENT NO. : 6,638,976 B2
DATED : October 28, 2003
INVENTOR(S) : Gamache et al.

It is certified that error appears in the above-identified patent and that said Letters Patent is hereby corrected as shown below:

Title page,
Item [57], ABSTRACT, change "3-benzolphenylacetic" to -- 3-benzoylphenylacetic --.

Signed and Sealed this

Thirty-first Day of May, 2005

JON W. DUDAS
*Director of the United States Patent and Trademark Office*